United States Patent [19]
Scott

[11] Patent Number: 5,192,408
[45] Date of Patent: Mar. 9, 1993

[54] ELECTROPHORESIS GEL SEALING GASKET AND SYSTEM

[75] Inventor: Charles B. Scott, Rancho Santa Fe, Calif.

[73] Assignee: CBS Scientific, Inc., Del Mar, Calif.

[21] Appl. No.: 750,826

[22] Filed: Aug. 27, 1991

[51] Int. Cl.⁵ ............................................. G01N 27/26
[52] U.S. Cl. ................................ 204/182.8; 204/299 R
[58] Field of Search .......................... 204/182.8, 299 R

[56] References Cited
U.S. PATENT DOCUMENTS 4,385,974  5/1983  Shevitz ............................. 204/182.9
4,772,373  9/1988  Ekata ................................. 204/182.8

*Primary Examiner*—John Niebling
*Assistant Examiner*—David G. Ryser
*Attorney, Agent, or Firm*—Gray, Cary, Ames & Frye

[57] ABSTRACT

Disclosed is a gasket, system and method for forming and sealing an electrophoresis gel casting chamber by utilizing a sealing gasket having a plate retention channel and an integral sealing gasket portion. The gel casting chamber system includes electrophoresis gel plates and spacers which are particularly adapted for use with the disclosed gasket.

23 Claims, 2 Drawing Sheets

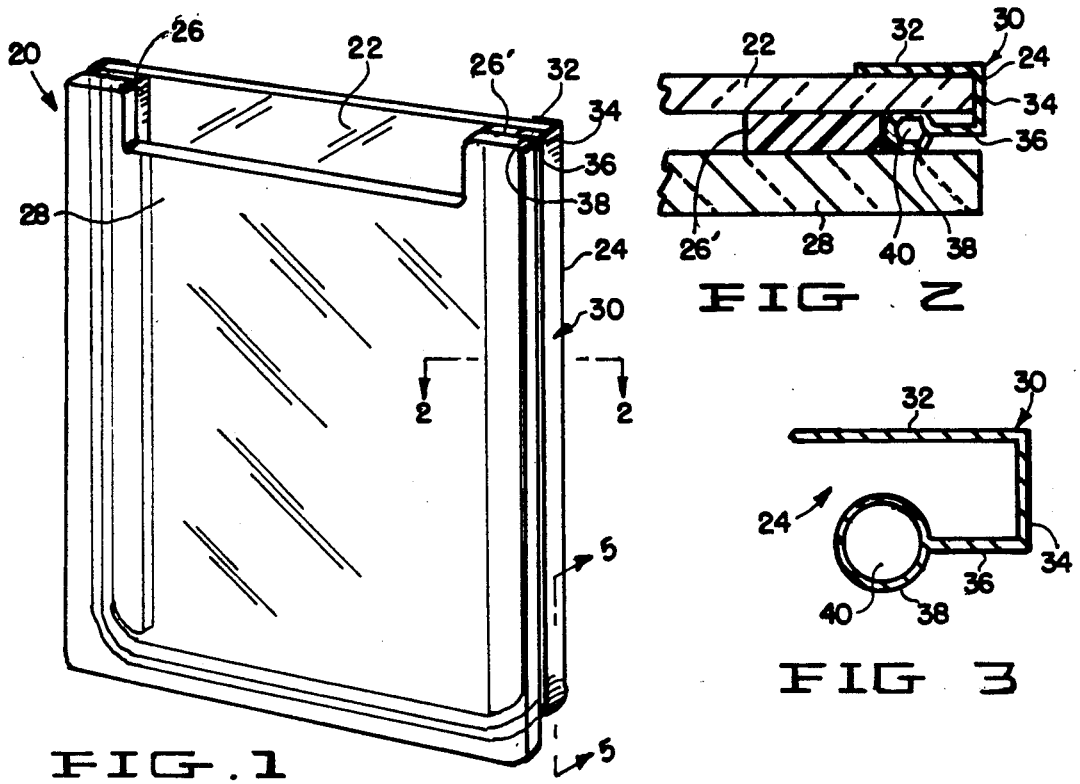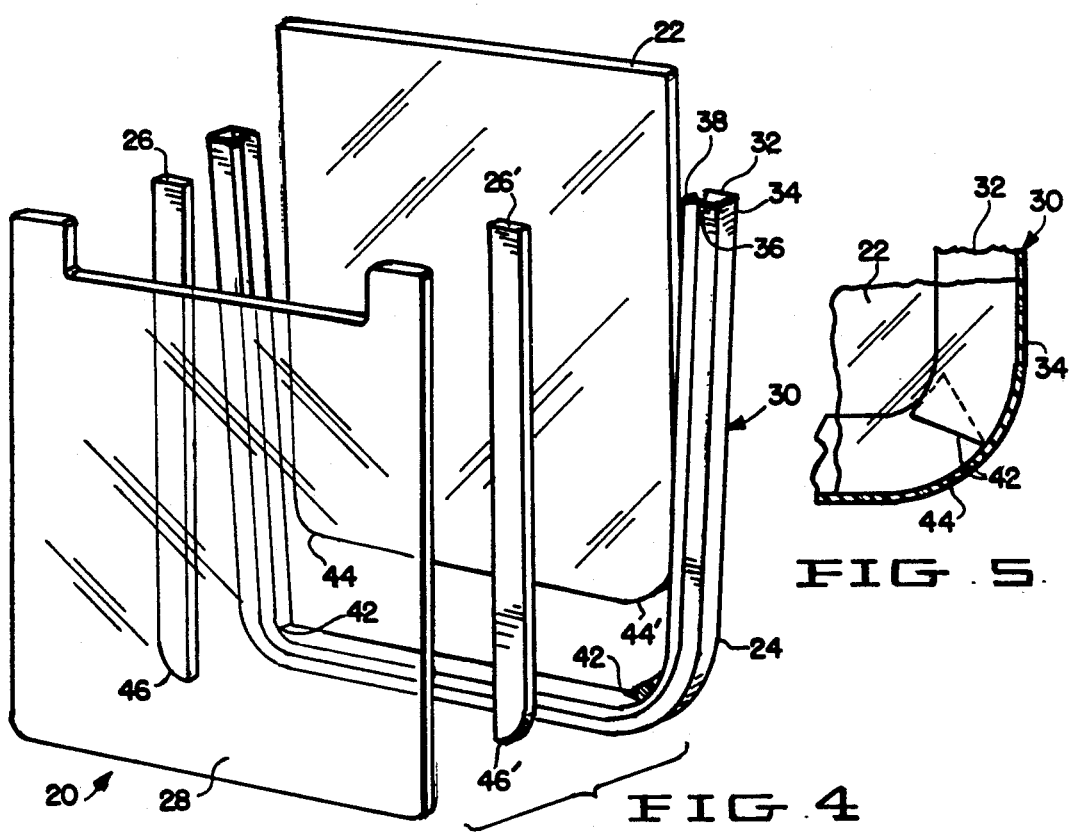

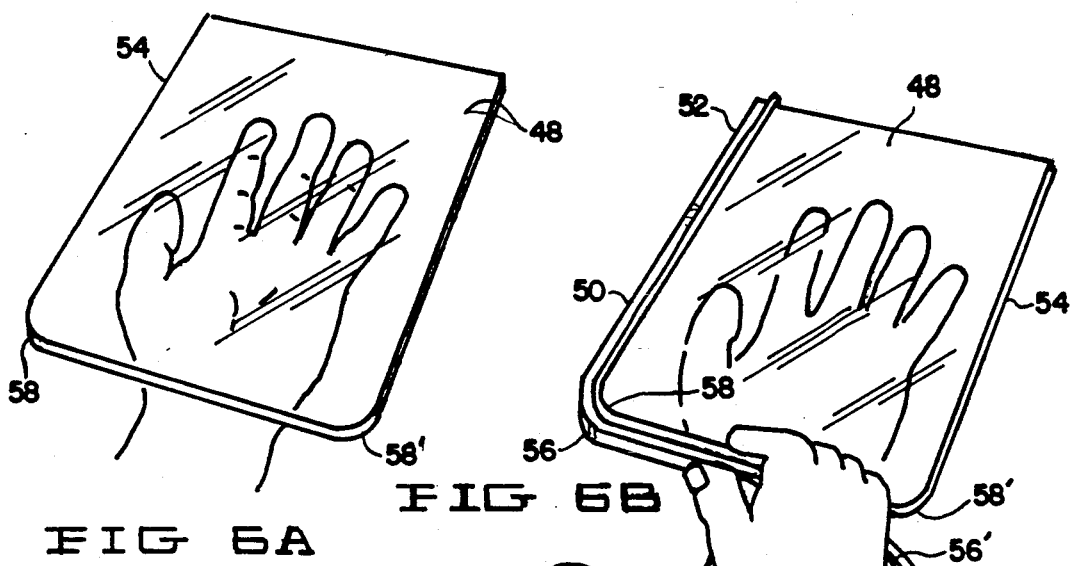
FIG 6A
FIG 6B
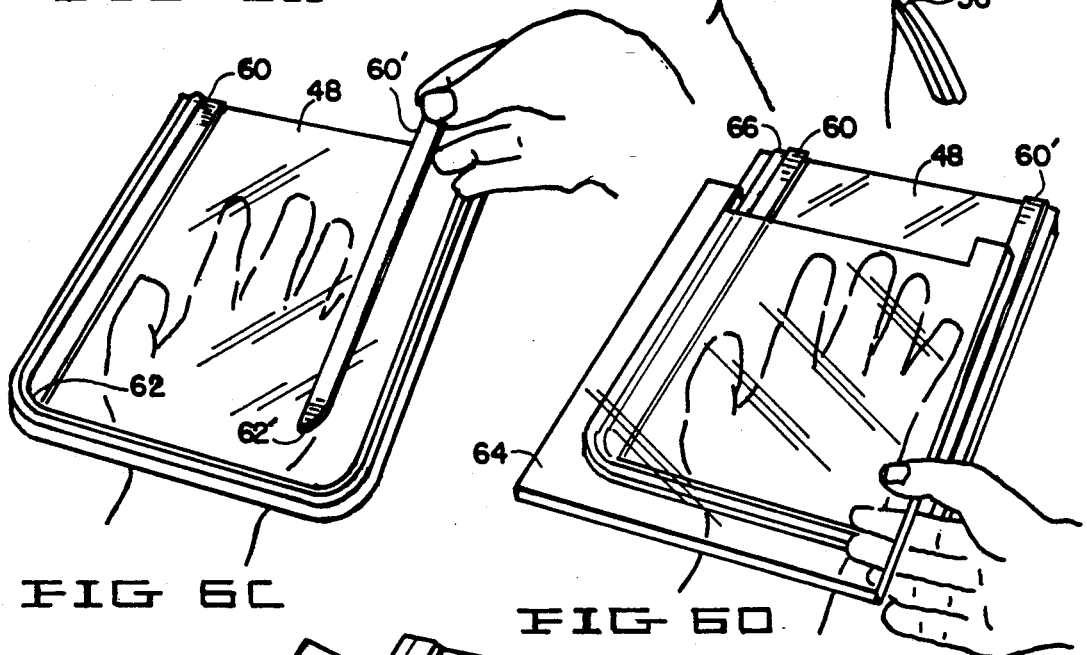
FIG 6C
FIG 6D
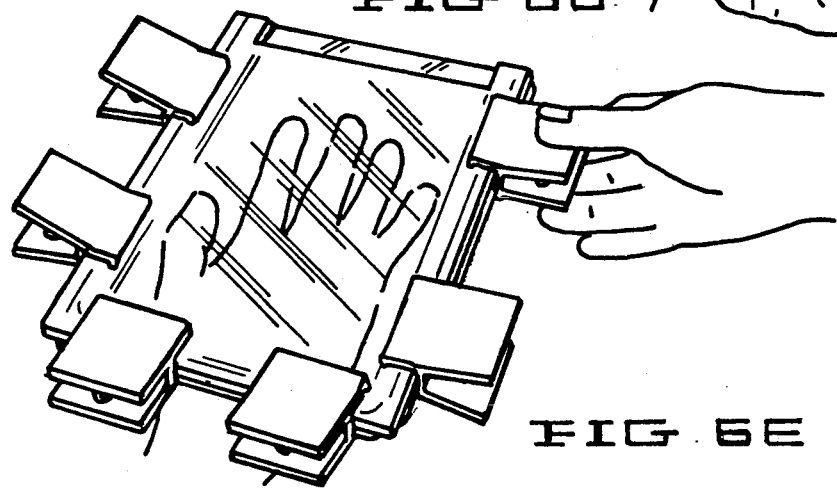
FIG 6E

ELECTROPHORESIS GEL SEALING GASKET AND SYSTEM

DESCRIPTION

1. Field of the Invention

The present invention relates generally to electrophoresis gel casting methods and apparatus and, more particularly, to sealing a slab gel chamber while casting the gel.

2. Background of the Invention

The methodologies known collectively as electrophoresis involve the migration of charged molecules through a suitable restraining medium under the influence of an electric field. Generally, assuming approximately uniform charge-to-mass ratios and conformation, molecules of higher molecular weight migrate at a slower rate through the medium than molecules of lower molecular weight.

The restraining medium utilized in electrophoresis is most often a form of gel, which consists of a matrix structure in a suitable solvent. Commonly used gels include agarose, starch and polyacrylamide, among others. In a number of methodologies, the gel is cast in an appropriate chamber preparatory to sample addition and the application of an appropriate electric field. Such chambers define the shape of the resulting gel, with tube gels and both horizontal and vertical slab gels being the most commonly employed.

In slab electrophoresis gels, the gel is usually cast in a chamber created by an apposing pair of glass plates. These plates are separated at a defined distance using spacers and the edges of the chamber are temporarily sealed, so that the void created can be filled with a liquid gel-forming solution without leakage. The sealing requirement is usually temporary, as the gel liquid will change state, e.g. by chemical polymerization (acrylamide) or cooling (agarose) to form a gel solid.

Leaks in the chamber seal adversely effect the formation of a useful gel. For example, many gel media require the exclusion of air from contact with the solution, because air contamination will prevent polymerization of the gel. Also, leaks may create nonuniform gel volumes. Thus, leaks in the chamber during gel casting lead to the creation of improper gel formations which ultimately lead to inefficient and ineffective separation of the compounds during electrophoresis. Typically, the solution to an improperly formed gel requires that the resulting gel be discarded.

Since the first publication of slab gel techniques, operators have employed various methods to temporarily secure three of the four sides of the "sandwich" formed between the glass plates. Representative of traditional methodologies for preparing vertical slab gels is U.S. Pat. No. 3,932,265. Although many of the sealing techniques have been successful, they are often time consuming to set up and clean, or are messy and unreliable.

Virtually all early attempts to seal the gel casting chamber employed three spacers: two side spacers and one for the bottom of the chamber. The side spacers remained in place after gel formation whereas the bottom spacer was removed to allow electrical conductance through the gel. Using three spacers, operators have coated each spacer with silicon grease lubricant prior to clamping the chamber. While generally effective, this grease seal technique requires a substantial amount of cleanup, especially of the glass plates.

Alternatively, hot agarose has been applied via pipettes along the inside and outside edges of the sandwich, in order to seal the gel casting chamber. However, substantial time is required to make up the agarose solution in appropriate buffer and for the agarose to cool before a gel can be cast.

Early efforts involving the use of only two side spacers would combine either grease or agarose along the sides and modeling clay or agarose plugs to seal the bottom edge of the chamber. Subsequently, a slightly oversized length of silicone tubing was employed which could be forced between the sandwiched glass plates as a gasket perimeter. Others have designed a clamp which could compress the side spacers and press the glass sandwich onto a silicone pad to seal the bottom.

Various attempts have been made to provide improved equipment for such gel casting and electrophoresis including U.S. Pat. Nos. 4,290,871, 4,224,134 and 4,325,796.

While many of the techniques were successful in sealing the gel chamber, none could be performed quickly, reliably and without expensive clamping mechanisms. Although simpler than other techniques, the use of a length of silicone tubing as a sealing gasket had a major drawback: in order to provide an effective seal, the silicone tubing is generally employed in diameters approximately 0.020 inches thicker than the spacers. However, the tubing must be inserted between the glass plates next to the spacers in order to provide the gasket seal. The insertion of the appropriate size tubing is not technically difficult, but requires a degree of skill, coordination and patience. Supplemental tools have been employed to press the tubing between the plates; often applying too much pressure and thereby displacing the spacers and necessitating adjustments.

Therefore, the technique of the operator often plays an essential role in the gel casting process in order to provide a sealed chamber that is leak-proof. In some cases it may require an entire day to set up the chamber and cast the gel, so that valuable time is lost when a system develops leaks and the resulting gel must be discarded. Also, many of the sealing materials presently in use are not recoverable or reusable.

It has long been recognized that the casting of a gel and subsequent setup for performing electrophoresis can require complex equipment or operational manipulations for which simplification is always desirable from an operator's standpoint.

It is therefore considered desirable to provide a sealing gasket that is a significant improvement over the prior art in preventing leaks. It is also considered desirable to provide a seal that is easily and quickly adapted to a gel electrophoresis chamber with the resulting savings in time and cost.

DISCLOSURE OF THE INVENTION

This invention provides a novel and improved gasket, system and method for forming and sealing an electrophoresis gel casting chamber by utilizing a sealing gasket which simplifies the set-up of the chamber and reduces the incidence of leaks, particularly with less skilled operators.

One aspect of the invention provides a gel casting chamber sealing gasket comprising an elongate deformable member comprising a plate retention channel integral with a gasket portion. The plate retention channel portion is adapted to conform to and releasable retain a portion of the edge of a first electrophoresis gel plate.

The elongate member also includes a gasket portion which is formed integral with the plate retention channel. The gasket portion is adapted to form a seal between the first gel plate and a second plate placed in close proximity therewith, thereby forming an electrophoresis gel casting chamber.

The present invention also includes a gel electrophoresis system which comprises a first substantially planar base plate having at least two adjacent substantially curvilinear corners. The system also comprises a sealing gasket in accordance with the invention and a plurality of spacers adapted to conform to the sealing gasket as applied to the gel plate.

The present invention also includes a method for forming electrophoresis gels in a chamber formed with a sealing gasket held between two apposing electrophoresis plates which includes the improvement of attaching a gel electrophoresis system gasket to an edge portion of a electrophoresis plate.

BRIEF DESCRIPTION OF THE DRAWINGS

FIG. 1 is a perspective view of an electrophoresis gel casting system embodying the present invention;

FIG. 2 is a cross sectional view of a portion of the system of FIG. 1 taken along line 2—2;

FIG. 3 is a cross sectional view of a sealing gasket embodiment of the present invention;

FIG. 4 is an exploded view of the gel casting system of FIG. 1;

FIG. 5 is a cross sectional view of a portion of the system of FIG. 1 taken along line 5—5; and FIGS. 6A-E are perspective views depicting the steps of carrying out a method of assembling a gel casting system of the present invention, in which:

FIG. 6A depicts a base plate of the present system preparatory to forming a casting chamber;

FIG. 6B depicts the attachment of a sealing gasket of the present system to the base plate of FIG. 6A;

FIG. 6C depicts the placement of a pair of spacers of the present system on the base plate/sealing gasket assemblage of FIG. 6B;

FIG. 6D depicts the placement of a top plate of the present system on the base plate/sealing gasket/spacer assemblage of FIG. 6C; and FIG. 6E depicts the placement of clamps to secure the base plate/sealing gasket/spacer/top plate assemblage of FIG. 6D.

DETAILED DESCRIPTION OF THE INVENTION

The present invention provides a novel and improved gasket, system and method for forming and sealing an electrophoresis gel casting chamber by utilizing a sealing gasket which simplifies the set-up of the chamber and reduces the incidence of leaks during gel casting.

One aspect of the invention provides a gel casting chamber sealing gasket comprising an elongate deformable member comprising a plate retention channel integral with a gasket portion. The plate retention channel portion is adapted to conform to and releasable retain a portion of the edge of a first electrophoresis gel plate. The elongate member also includes a gasket portion which is formed integral with the plate retention channel. The gasket portion is adapted to form a seal between the first gel plate and a second plate placed in close proximity therewith, thereby forming an electrophoresis gel casting chamber.

The present invention also includes a gel electrophoresis system which comprises a first substantially planar base plate having at least two adjacent substantially curvilinear corners. The system comprises a sealing gasket in accordance with the invention and, optionally, a plurality of spacers adapted to conform to the sealing gasket as applied to the gel base plate.

As an overview, FIGS. 1 and 4 of the Drawings illustrate an embodiment of the gasket and system of the present invention. As depicted in FIG. 1, assembled gel casting system 20 comprises individual components as depicted in greater detail in FIG. 4. These components include base plate 22 and sealing gasket 24 and, optionally, spacers 26, 26' and top plate 28. Each of the individual components will be described in detail below.

An embodiment of the sealing gasket 24 of the present invention is an elongate deformable member, desirably constructed as a plastic extrusion. One plastic which has been found to be particularly advantageous is silicone, due to its desirable properties of deformability, resilience, lack of reactivity with the agents used to cast and run electrophoresis gels, and its low cost.

Embodiments of the present gasket have been constructed as silicone extrusions by Specialty Silicone Fabricators, Inc. (Paso Robles, CA) using a proprietary formulation (SSF-METD-750) which was considered to optimize a combination of these desirable properties. The material specifications of this silicone formulation are reported to include:

| Description | Units | Specification Limits | |
| --- | --- | --- | --- |
| | | Low | High |
| Specific Gravity | | 1.13 | 1.16 |
| Durometer-Shore A | | 45 | 55 |
| Tensile Strength (at break) | psi | 1200 | Minimum |
| Elongation (at break) | % | 750 | Minimum |
| Tear (Die B) | ppi | 200 | Minimum |

However, the above formulation is probably only one of many which will be found suitable for the practice of the invention and it is expected that other gasket embodiments can also be constructed (for example in accordance with Dow-Corning specification RX-50) which may emphasize one or more desirable features for particular applications, in accordance with the ordinary skill in manufacturing such silicone plastics.

As can be seen most clearly from FIG. 3, sealing gasket 24 is comprised of a plate retention channel portion 30 comprising a first side 32, bottom side 34 and second side 36, which channel is adapted to conform to and releasable retain a portion of the edge of substantially planar base plate 22. With the planar, quadrilateral glass plates commonly used to form electrophoresis slab gel chambers, the plate retention channel portion of sealing gasket 24 will desirably have a substantially "J-shaped" cross section to enclose the edge of the plate.

The retention channel may vary in size and shape. Thus, retention channel 30 may be J-shaped, U-shaped or L-shaped. The retention channel can also be rigid or a substantial deformable variation of the above-described shapes. Furthermore, the retention channel need not extend continuously along the length of the deformable member in order to practice the invention. The retention channel functions primarily to hold the seal in place during the insertion of the plates, thus allowing for ease of gel chamber formation. Therefore, the channel need only extend sufficiently along the gasket so as to perform this function.

Formed integral with the second side 36 of plate retention channel 30 is the gasket portion 38 of the sealing gasket 24, which portion is adapted to form a seal between a face of the base plate 22 and a face of a substantially planar top plate 28 placed in close proximity thereto, thereby forming a casting chamber.

In one embodiment, formed integral means that the present gasket is formed of one piece. Thus, such an embodiment discloses sealing gasket 24 where plate retention channel 30 and gasket portion 38 are formed of one piece cast or extruded from a single die. However, the phrase formed integral is not restricted to an embodiment constructed of one piece. Formed integral also means to continue and to complete. Therefore, other embodiments are contemplated where the channel portion may be formed of one material and attached to the gasket portion formed from a second material. The particular features of the present invention, for example the retention channel and the gasket portion, may, for example, be glued together, chemically bonded, or heat sealed. Thus, formed integral means that the retention channel and the gasket portion are of a continuous and complete form regardless of how they are connected and regardless of the specific material used to construct each element.

Although depicted in FIG. 3 in circular cross section, and thus cylindrical configuration, the gasket portion could be formed as any of numerous cross sections while providing the sealing capability inherent in the present gasket. The gasket portion may vary in size and shape to permit its use in forming gels of various volumes and thicknesses. The gasket portion may be shaped in any manner sufficient to provide an effective seal of the electrophoresis system. For example, the gasket portion may be substantially triangular or substantially rectangular.

In order to improve the compressibility, and thus the sealing ability, of the gasket, the gasket portion 38 can include an inner hollow channel 40 extending the entire length of the gasket portion.

As shown in FIG. 2, the gasket portion will generally be of a size exceeding the thickness of the spacer selected to form the gel casting chamber, so as to maximize the sealing capabilities upon assembly. As shown in the following table, different sizes of the gasket portion will be found useful in forming a desired gel thickness.

TABLE 1

| Gel Thickness (in mm) | Gasket Dimensions (in inches) | |
|---|---|---|
| | I.D. | O.D. |
| 0.75 mm | 0.025 | 0.047 |
| 1.0 mm | 0.030 | 0.065 |
| 1.5 mm | 0.040 | 0.085 |
| 2.0 mm | 0.062 | 0.095 |
| 3.0 mm | 0.062 | 1.45 |

As also shown in FIG. 4, the elongate sealing gasket will generally be of sufficient length to enclose approximately three sides of the base plate 22 used to form the gel casting chamber.

As shown in FIG. 5, the present sealing gasket can also include a structurally imposed feature 42 which allows the sealing gasket to conform more closely to the shape of the baseplate when the two are joined in an assembly. In one embodiment, the feature can be as simple as a slit or wedge-shaped void at a location on the channel portion of the gasket which approximates the corner of the baseplate when the sealing gasket is installed. Such a feature reduces the tendency of the sealing gasket to buckle when fitted around a corner, thus reducing the tendency of the gasket portion to lift away from the face of the baseplate.

Alternatively, a sealing gasket in accordance with the present invention could be formed in a overall shape adapted to approximate the perimeter of base plate 22.

In alternate embodiments of the present invention, one can utilizing a sealing gasket having a dual channel system. For example, a first channel will have a side wall, a bottom wall, and a middle wall. A second channel will have a second side wall, a second bottom wall, and will share the middle wall with the first channel. The gasket portion will be situated on top of the middle wall and extend along an axis parallel to the channels. In this embodiment, both plates comprising the casting chamber will be retained by the sealing gasket.

Another embodiment of the invention contemplates the use of a material which is lined within and throughout the inner walls of the channel. An example of this would be a metal material such as lead enclosed within the walls of the channel. This feature allows the retention channel to retain its shape and permits it be firmly secured to the plates.

An embodiment of base plate 22 in accordance with the present invention will usually include slight modifications from conventional base plates previously used to form gel casting chambers. In particular, as shown in FIGS. 4 and 5, the corners 44, 44' of base plate 22 which will be fitted into retention channel 30 are desirably relieved to form substantially curvilinear corners. Such a configuration for the base plate facilitates the installation of the sealing gasket to the plate and further reduces the tendency of the gasket to buckle upon installation. In a preferred embodiment, a radius of approximately 1.125 inches has been found particularly desirable. The preferred radius of the corners may vary according to the thickness of the base plate. In certain embodiments, the curvilinear corners of a base plate embodiment will have dimensions as follows: Approximately a 1 inch radius for a mini gel system, where the plates typically have a thickness of less than approximately 0.125 inches; approximately a 1.125 inch radius for large gel systems using plates having a thickness of approximately 0.125 inches; and approximately a 1.25 inch radius for gel systems using plates having a thickness of approximately 0.1875 inches. This feature, in conjunction with the above-described adaptation of the sealing gasket enables the gasket to be easily applied without any tendency to form voids in the gasket seal.

In addition, the system of the present invention desirably includes a plurality of spacers 26, 26' which are optionally adapted to conform more closely to the shape of the sealing gasket when installed on the baseplate. As shown in FIG. 4, these adaptations can include substantially curvilinear corners 46, 46' on one end of each spacer, which allows the spacer to fit closely to the sealing gasket, as shown in FIG. 1.

The present system will also utilize certain components well known in the art, including a top plate 28 configured to appose the present base plate 22, and some means of clamping the system together preparatory to gel casting. Clamps, such as are depicted in FIG. 6E, will generally prove adequate for this purpose.

The present invention also includes a method for forming electrophoresis gels in a casting chamber formed with a the present sealing gasket held between two apposing plates, which includes the improvement of attaching a sealing gasket to an edge portion of at least one plate.

FIGS. 6A-E illustrate a method for forming a gel casting chamber utilizing the system and gasket of the present invention. As shown in FIG. 6A, base plate 48 is first held in one hand of the operator.

FIG. 6B shows how the operator attaches the sealing gasket 50 by sliding plate retention channel 52 over edge 54 of plate 48. In certain embodiments, the structurally imposed features 56, 56', used to enhance the fit of the gasket 50, will be approximately aligned with corners 58, 58' of plate 48.

In FIG. 6C, the gasket 50 is shown as fitting around three sides of the perimeter of plate 48. The operator then places spacers 60, 60' so that they are aligned with the edges of plate 48. In certain embodiments, spacers 60, 60' will be provided with substantially curvilinear corners 62, 62' so as to allow the spacers to be placed as close to the edge 54 of the plate as possible.

As shown in FIG. 6D, top plate 64 is then placed directly over base plate 48, contacting spacers 60, 60' and the gasket portion 66 of sealing gasket 50. Then, as seen in FIG. 6E, the complete chamber is clamped together using conventional clamps for subsequent use.

Thus, the present invention allows for the rapid formation of a leak-proof gel chamber without the need for lengthy preparation or messy seals.

Although described primarily with reference to vertical slab gel casting, the present invention is not restricted to such use, as it will be readily applicable in any system that contemplates the use of at least two apposing plates to form a casting chamber.

It will be apparent to those skilled in the art that a number of other variations and modifications may be made in this invention without departing from its spirit and scope. The description as set out above is only illustrative and is not limiting.

I claim:

1. An electrophoresis gel casting chamber sealing gasket comprising an elongate deformable member comprising:
    a plate retention channel portion adapted to conform to and releasably retain a portion of the edge of a substantially planar base plate; and
    a gasket portion formed integral with said plate retention channel portion and adapted to form a seal between a face of said base plate and a face of a substantially planar top plate placed in close proximity thereto, thereby forming a gel casting chamber.

2. The sealing gasket as recited in claim 1 wherein said elongate member is of a length sufficient to encompass approximately three edges of said base plate.

3. The sealing gasket as recited in claim 1 wherein said elongate member comprises a silicone extrusion.

4. The sealing gasket as recited in claim 1 wherein the cross-section of the exterior of said gasket portion is substantially circular.

5. The sealing gasket as recited in claim 1 wherein said gasket portion is substantially hollow.

6. The sealing gasket as recited in claim 1, said plate retention channel portion further comprising:
    a structurally imposed means for allowing said channel to substantially conform to a corner of said base plate while reducing the tendency of said gasket portion to lose contact with the face of the base plate.

7. The sealing gasket as recited in claim 6 wherein the structurally imposed means comprises a void located on the gasket at a position corresponding to said corner wherein the void prevents bunching and wrinkling of said gasket.

8. The sealing gasket as recited in claim 1 further comprising:
    a second plate retention channel portion located adjacent and approximately parallel to said first plate retention channel portion and adapted to conform to and releasably retain a portion of said second electrophoresis gel plate in close proximity to said first electrophoresis gel plate.

9. An electrophoresis gel casting chamber sealing gasket comprising a flexible elongate extrusion which includes a compressible, substantially cylindrical, hollow gasket portion integrally formed with a substantially "U-shaped" plate retention channel, wherein said gasket portion is sized for insertion between the inner faces of a pair of spaced, apposing substantially planar plates, and wherein said plate retention channel is adapted to conform to and releasably retain a portion of the edge of one of the plates and wherein said gasket portion is formed integrally with a side of said channel such that the gasket portion is retained in contact with a face of the plate enclosed in the plate retention channel.

10. An electrophoresis gel casting chamber system comprising:
    a first substantially planar plate having at least two adjacent substantially curvilinear corners; and
    a sealing gasket comprising an elongate deformable member comprising:
        a plate retention channel portion adapted to conform to and releasably retain a portion of the edge of said first plate including said curvilinear corners; and
        a gasket portion formed integral with said plate retention channel portion and adapted to form a seal between said first plate and a second substantially planar plate placed in close proximity thereto, thereby forming an electrophoresis gel casting chamber.

11. The system as recited claim 10 further comprising:
    a structurally imposed means for forming said channel to substantially conform to the corners of said first plate.

12. The system as recited in claim 11 wherein the structurally imposed means comprises a void located on the gasket at a position corresponding to said corners wherein the void prevents bunching and wrinkling of said gasket.

13. The system as recited in claim 10 further comprising:
    a plurality of spacers adapted to maintain said first and second plates at a predetermined distance when said plates are placed in close proximity, thereby forming an electrophoresis gel casting chamber.

14. The system as recited in claim 13 wherein the spacers each comprise a means for substantially conforming to the corners of said first plate.

15. In a method for forming electrophoresis gels in a chamber formed with a sealing gasket held between two apposing substantially planar plates, the improvement comprising:

providing a sealing gasket which is capable of substantially conforming to and releasably retaining a portion of an edge portion of at least one substantially planar plate.

16. The method as recited in claim 15 wherein the sealing gasket comprises:

a plate retention channel portion adapted to conform to and releasably retain a portion of the edge of a first electrophoresis gel plate; and a gasket portion formed integral with said plate retention channel portion and adapted to form a seal between said first electrophoresis gel plate and a second electrophoresis gel plate placed in close proximity thereto, thereby forming an electrophoresis gel casting chamber.

17. The method as recited in claim 15 wherein said gasket comprises:

a flexible and reusable silicone extrusion formed to include a substantially cylindrical, hollow gasket, wherein said gasket is sized for insertion between the outer edges of electrophoresis plates, wherein said gasket is compressible to allow for maximum seal and fit during the formation of electrophoresis gels, said extrusion further comprising a channel, said channel having a first side, a second side, and a bottom side, said first side connected at its end to said gasket such that the channel encloses the edge of a electrophoresis plate when said gasket is inserted between electrophoresis plates during the formation of electrophoresis gels.

18. The method as recited in claim 15 wherein the gasket comprises:

a length of flexible material having a substantially U-shaped electrophoresis plate-enclosing channel, said channel defined by a first side, a second side, and a bottom side, said second side smaller in height then said first side, wherein said channel is sized to enclose an electrophoresis plate;

a gasket portion formed integral on top of said second side and extending along the length of said second side, parallel to said channel, wherein said gasket is sized to fit between two electrophoresis plates.

19. In a method for forming electrophoresis gels in a chamber formed from two apposing electrophoresis plates, the improvement comprising:

attaching a gel electrophoresis system gasket to the edge portion of electrophoresis plates by inserting each of said plates into separate plate retention channels which channels are formed integral with said gasket and adapted to conform to and releasably retain said plate edges.

20. The method as recited in claim 19 wherein the gasket comprises:

a plate retention channel portion adapted to conform to and releasably retain a portion of the edge of a first electrophoresis gel plate;

a gasket portion formed integral with said plate retention channel portion and adapted to form a seal between said first electrophoresis gel plate and a second electrophoresis gel plate placed in close proximity thereto, thereby forming an electrophoresis gel casting chamber; and a second plate retention channel portion located adjacent and approximately parallel to said first plate retention channel portion and adapted to conform to and releasably retain a portion of said second electrophoresis gel plate in close proximity to said first electrophoresis gel plate.

21. In a method for forming electrophoresis gels between a space formed from two apposing electrophoresis plates, the improvement comprising:

sealing said space with a seal, said seal comprising:

a flexible and reusable silicone extrusion formed to include a substantially cylindrical, hollow gasket, wherein said gasket is sized for insertion between the outer edges of electrophoresis plates, wherein said gasket is compressible to allow for maximum seal and fit during the formation of electrophoresis gels, said extrusion further comprising a channel, said channel having a first side, a second side, and a bottom side, said first side connected at its end to said gasket such that the channel encloses the edge of a electrophoresis plate when said gasket is inserted between electrophoresis plates during the formation of electrophoresis gels.

22. The method as recited in claim 21 wherein said gel is formed in a vertical electrophoresis gel system.

23. The method as recited in claim 21 wherein said gel is formed in a horizontal electrophoresis gel system.

* * * * *